US006464392B1

United States Patent
Carrieri et al.

(10) Patent No.: US 6,464,392 B1
(45) Date of Patent: Oct. 15, 2002

(54) TACTICAL THERMAL LUMINESCENCE SENSOR FOR GROUND PATH CONTAMINATION DETECTION

(75) Inventors: Arthur H. Carrieri, Abingdon, MD (US); Irving F. Barditch, Baltimore, MD (US); David J. Owens, Baltimore, MD (US); Erik S. Roese, Baltimore, MD (US); Pascal I. Lim, Baltimore, MD (US); Michael V. Talbard, BelAir, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/546,742

(22) Filed: Apr. 11, 2000

(51) Int. Cl.$^7$ .............................................. G01N 25/72
(52) U.S. Cl. .............................. 374/45; 374/124; 374/5
(58) Field of Search ................................ 374/4, 5, 6, 7, 374/45, 124; 250/253, 301; 89/1.13

(56) References Cited

U.S. PATENT DOCUMENTS

| | | | | |
|---|---|---|---|---|
| 3,427,861 A | * | 2/1969 | Maley | 374/5 |
| 3,899,213 A | * | 8/1975 | Fantasia et al. | 250/301 |
| 4,236,071 A | * | 11/1980 | Chimenti | 250/253 |
| 4,247,770 A | * | 1/1981 | Welch | 250/253 |
| 4,496,839 A | * | 1/1985 | Bernstein et al. | 250/341.6 |
| 4,516,158 A | * | 5/1985 | Grainge et al. | 348/145 |
| 5,228,776 A | * | 7/1993 | Smith et al. | 374/5 |
| 5,241,179 A | | 8/1993 | Carrieri | |
| 5,417,494 A | * | 5/1995 | Kempa et al. | 374/5 |
| 5,631,469 A | | 5/1997 | Carrieri et al. | |
| 5,742,053 A | * | 4/1998 | Rekunyk | 250/338.5 |
| 6,343,534 B1 | * | 2/2002 | Khanna et al. | 102/402 |

* cited by examiner

Primary Examiner—Diego Gutierrez
Assistant Examiner—Lydia M. De Jesús
(74) Attorney, Agent, or Firm—Ulysses John Biffoni; Herbert Rose

(57) ABSTRACT

Chemical agent warfare materials and their simulant liquids are identified on terrestrial surfaces at a distance by recognizing the contaminant's infrared fingerprint spectrum brought out in thermal luminescence (TL). Suspect surfaces are irradiated with microwave light that is absorbed into the surface and, subsequently, TL is released by the surface. An optics receiver collects the released TL radiant light, and a data acquisition system searches this TL radiant flux for the contaminant's fingerprint infrared spectrum. A decision on the presence or absence of any-of-N contaminants is done by a neural network system that acts as a filter through real-time pattern recognition of the contaminant's unique infrared absorption or emission spectra.

35 Claims, 5 Drawing Sheets

TACTICAL THERMAL LUMINESCENCE SENSOR FOR GROUND PATH CONTAMINATION DETECTION

GOVERNMENT INTEREST

The invention described herein may be manufactured, licensed, and used by or for the U.S. Government.

BACKGROUND OF THE INVENTION

1. Field of the Invention

The present invention relates to a thermal luminescence (TL) sensor system for tactical military deployment, referred herein as a Tactical Thermal Luminescence Sensor system, and abbreviated as TTLS. More particularly, the present invention identifies chemical agent warfare materials and their simulant liquids on terrestrial surfaces at a distance by recognizing the contaminant's infrared fingerprint spectrum brought out in thermal luminescence. Most particularly, the TTLS device irradiates a suspect surface with microwave or near IR light that is absorbed into the surface and, subsequently, TL is released by the surface. An optics receiver collects the released TL radiant light and, at the most opportune irradiation time, a data acquisition system searches this TL radiant flux for the contaminant's fingerprint infrared spectrum. A decision on the presence or absence of any-of-N contaminants is done by a neural network system that acts as a filter through real-time pattern recognition of the contaminant's unique infrared absorption or emission spectrum.

2. Brief Description of the Related Art

In military maneuvering and industrial cleanup operations it is often vital to rapidly ascertain the presence and extent of land area chemical contamination caused by deliberate or accidental spill. Passive radiometry cannot detect liquids on a surface by infrared spectroscopy if the contaminant and its medium are in thermal equilibrium, or even in a quasi-thermal equilibrium state. An ambient thermal spectrum by the interstitial contaminant mass cannot be revealed, as it is a negligible small signal superimposed on the medium's overall Graybody spectrum, lying well inside the noise level of standard radiometer instrumentation.

Presently, a threat liquid mass on a surface is neutralized for the safeguard of life and health with ground maps, in hand, that outline the presence of specific compounds and their surface/volume coverage. There is a need in the art for remotely detecting and identifying classes of suspect contaminants on a surface area while providing rapid and safe monitoring. The present invention addresses this and other needs.

SUMMARY OF THE INVENTION

The present invention includes an apparatus for determining chemical contamination of terrestrial landscapes and manmade surfaces from the analysis of induced thermal spectra by employing thermal luminescence. The thermal luminescence is produced using a high power beam, wherein the beam frequency is selected from the group consisting of microwave and near infrared, where the frequency lies outside the mid infrared detection bandwidth and is efficiently absorbed by the irradiated surface. The TTLS has the means for collecting these liberated thermal emissions, means for processing collected liberated thermal emissions, and means for deriving pattern recognition stages from the processed thermal emissions.

The present invention also includes a method for determining chemical contamination of terrestrial landscapes and manmade surfaces, comprising the steps of irradiating a surface with a high powered beam, collecting liberated thermal emissions, processing the collected liberated thermal emissions and deriving pattern recognition stages from the processed thermal emissions.

The standoff detection system of the present invention identifies chemical contamination on terrain from a moving platform, such as a vehicle. An intense microwave beam emitting in the W-band region irradiates a slightly wet terrestrial surface for several seconds at approximately 1.5 $W\ cm^{-1}$ beam intensity or less. Liberated thermal emissions are reflected, condensed, and sent to a scanning interferometer for spectral processing. The interstitial liquid mass can be identified through its infrared band structure through a simple difference-spectrum of the thermal luminescence. Measurement of the thermal luminescence is timed to occur when the surface temperature gradient peaks, giving a state of maximum emissivity contrast between the ground and the thermally excited liquid. This allows for optimum detection of an onset of the contaminant's thermal spectrum. Generally, with the determination of a chemical contaminant, a warning, mapping or other corrective measures are taken.

DETAILED DESCRIPTION OF THE PREFERRED EMBODIMENTS

The present invention includes an apparatus, referred to herein as a Tactical Thermal Luminescence Sensor (TTLS) system, and a method that remotely identify chemical agent warfare materials and their simulant liquids on terrestrial surfaces by recognizing the contaminant's infrared fingerprint spectrum brought out in thermal luminescence (TL). The TL sensor detects simulants of liquid chemical nerve and blister agents, and similar organic compounds, wetting the ground in situ. With the irradiation of a suspect surface with microwave light, TL is released concomitantly by the surface. TL measurement occurs through the sensor's optic and electronic integrated components, capturing the released TL radiant light from the surface through an optics receiver. A data processing system searches the captured TL radiant flux for the contaminant's fingerprint infrared spectrum. A neural network determines the presence or absence of any-of-N contaminants, acting as a filter through real-time pattern recognition of the contaminant's unique infrared absorption or emission spectra. The data acquisition and reduction procedures and the neural network pattern recognition allow a real-time detection and identification decision through the presence or absence of thermal spectra in the TL radiant field, which may result in a warning alarm, mapping function, or other appropriate response to the contaminant threat.

Detection of the chemical contaminates occurs because water has a high absorption to an intense irradiating microwave beam emitting in the W-band region. With the irradiation of the wetted terrestrial surface by this beam, liberated thermal emissions between 700 and 1400 wavenumbers or $cm^{-1}$ are produced and subsequently directed to a scanning interferometer for spectral processing. By irradiating the slightly wet terrain for several seconds at approximately 1.5 W $cm^{-1}$ beam intensity, the interstitial liquid mass can be identified through its infrared band structure through a simple difference-spectrum of the thermal luminescence. This measurement is done inside a window where surface temperature gradient peaks: a state of maximum emissivity contrast between the ground and the thermally excited liquid.

Figure 1:
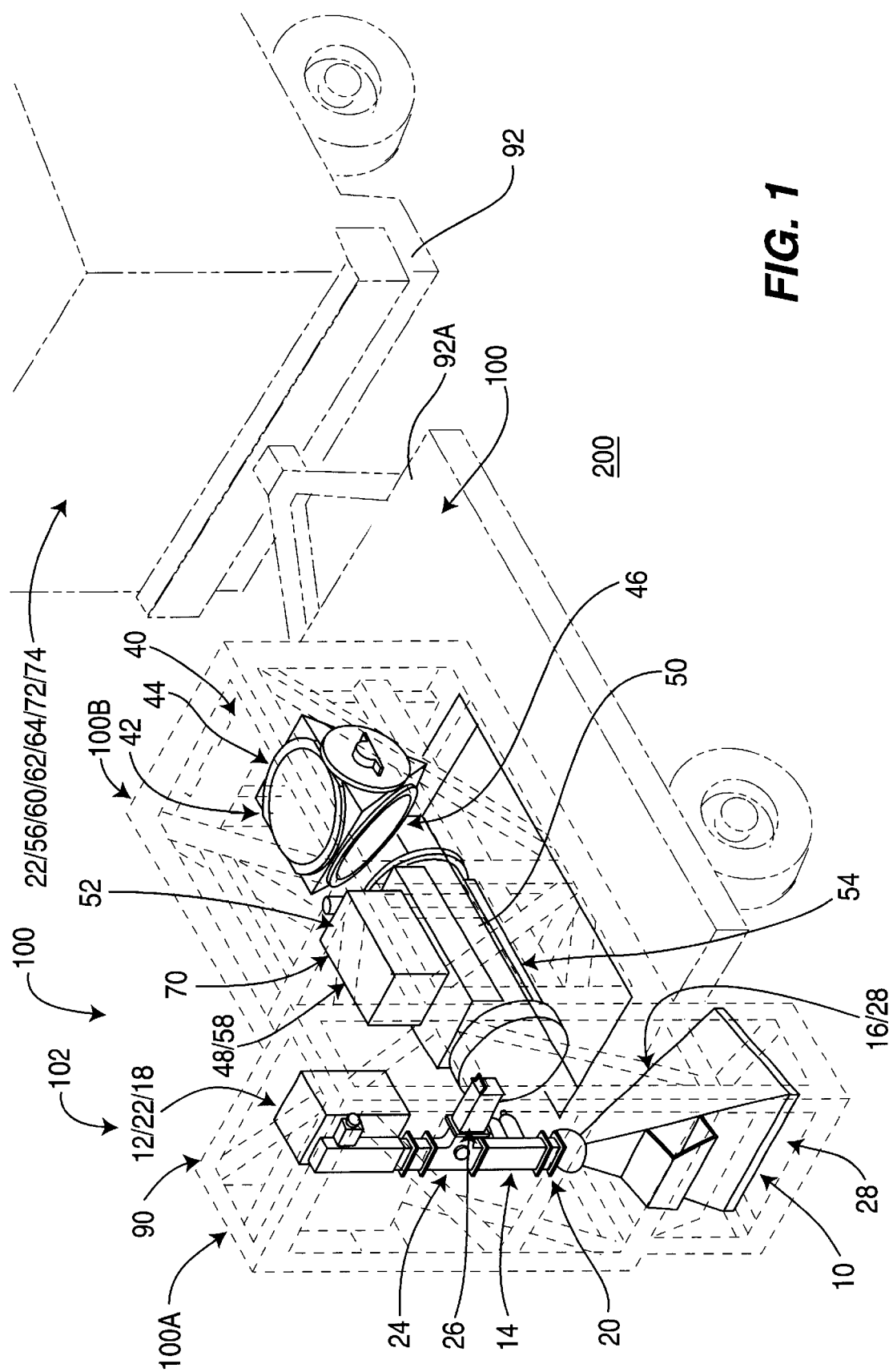
FIG. 1 shows the principal components of the present invention, including the housing assembly, scanner assembly, interferometer with beam condenser, magnetron, tuner and focusing horn.

Referring to FIG. 1, a standoff detection system or apparatus 100 of the present invention is shown. The apparatus 100 determines the presence of chemical contamination on terrestrial landscapes and/or manmade surfaces by analysis of induced thermal spectra from the surface contaminants 200. The apparatus 100 has a transmitter section 100A that employs thermal luminescence from a magnetron beam source 12 at the microwave 2.45 GHz frequency. Additionally, the apparatus 100 has receiver section 100B that uses a means to reflect and condense liberated thermal emissions 40 that result from the thermal luminescence on the surface contaminants 200. The condensed thermal emissions are processed by the apparatus 100 within a collection/analysis section 70 that has a means to process the condensed liberated thermal emissions 72. Processed thermal emissions are used to derive pattern recognition stages from the processed thermal emissions 74 that also is located in the collection/analysis section 70 of the apparatus 100.

The component parts of the apparatus 100 include an optical head structure 102 having a magnetron 12, beam condenser 50, rotating tri-mirror ground scanner 46 and fast-scan Michelson interferometer 52 arranged together in a housing assembly 90 to fix the relative position of each component relative to each other and other components. The housing assembly 90 includes a durable and rigid housing having inner and outer assemblies separated by vibration isolators. The vibration isolators provide for vibration damping so that the interferometer can operate within turbulent motion specification. The housing further comprises a sheet metal "skin" covering to protect the components of the apparatus 100 and provide environmental regulation of the enclosed volume. The isolators, along with additional dampeners, and air conditioning system allows the apparatus 100 to operate in a stable and climate-controlled environment during field testing and use.

External beam energy is absorbed into the ground volume, with a subsequent release of thermal emissions by the surface, yet all manifestations of that exact beam, i.e., scattering, are absent in the detector signal. By Kirchhoff's law, the ratio of absorptivity to emissivity of a heated radiator is constant, being independent of the type of material and dependent only on temperature of the medium, i.e., good absorbers and good emitters. The TTLS of the present invention exploits this relationship by irradiating the surface with a beam energy that coincides with an intense absorption line of water, which is present in terrain as water bearing materials. A microwave beam tuned to 2.45 GHz, the same energy commonly used for heating in a microwave oven cavity, meets this requirement.

Difference spectra are measured during the event where, in the beam irradiation zone, maximum thermal gradient is attained. This represents a thermodynamic state of peak emissivity contrast between analyte and background material. When the microwave beam is switched on, the emissivity contrast builds and then collapses in a period spanning incident beam exposure up until thermal equilibrium is attained at some elevated temperature. It is most prudent to capture the thermal radiance within this period when $\partial^2 T_s/\partial t^2 = 0$, where $T_s$ is surface temperature and t is irradiation time. A subtraction of spectra about this time reveals both absorption and emission bands of the contaminant layer without a need for elaborate background subtraction algorithms. The TTLS is designed to hone-in and search for the fingerprint spectra of multiple contaminants as the ground attains this state of stimulated flux, with minimum beam exposure time.

Resonant absorption of microwave energy into the ground with a concomitant release of broadband infrared emissions, i.e., thermal luminescence, by the surface occurs. The quantity of incident beam energy absorbed into the ground is inversely proportional to the time of beam irradiation required to separate the contaminant's thermal spectrum from the bulk Graybody spectrum, i.e., background, in the liberated thermal luminescence (TL) radiance.

Emissions by a heated random dielectric medium resemble a Gaussian type distribution within a range of from about 7.14–14.29 $\mu$m wavelengths of the middle infrared region of the electromagnetic spectrum. The peak emission amplitude lies in the neighborhood of 10.31 $\mu$m for soil at 23° C., and increases as a function of temperature whereby its corresponding frequency shifts towards higher energy. The approximately 7.14 $\mu$m to 14.29 $\mu$m band also includes the region where chemical agents and their simulants have strong and unique vibration spectra, giving the region where primary molecular groups of the analyte exhibit fundamental rock, wag, and stretch modes. The frequency location and intensity of these normal modes are unique characteristics of the chemical compound, and are collectively referred to as fingerprint spectra. The optical bandwidth of a Fourier Transform Infrared (FTIR) spectrometer system, used in the TTLS to dynamically collect and process TL, resides in the 7.14 $\mu$m to 14.29 $\mu$m region.

Transmitter Section 100A

The transmitter section 100A of the present invention comprises the beam source 10, a magnetron 12 for generating a 2.45 GHz frequency beam to be directed onto the surface contaminants 200. The source is not limited to this frequency beam. Near infrared lamps may be employed to generate the thermal luminescence. Generally, the irradiating beam is (1) strongly absorbed into the target material and (2) outside the mid infrared bandwidth of the TTLS detector element. Thus, high power beam source 10 functions at suitable wavelengths for contamination analysis as determinable by those skilled in the art, such as in the microwave W-band region or between a near infrared range of from about 2 $\mu$m to about 5 $\mu$m, or about 3 $\mu$m to about 4 $\mu$m. Higher ranges, such as from about 7.14–14.29 $\mu$m coincide with operating ranges of the interferometer 52, and are not appropriate. An example of the magnetron 12 is the Astek model S1500 magnetron, manufactured by ASTEX, Inc., of Woburn, Mass. The Astek model S1500 magnetron 12 provides up to 1500 watts of heating energy at 2.45 GHz.

The transmitter section 100A of the TTLS optical head 102 comprises a magnetron cavity 18 containing the magnetron 12 that emits W-band microwave radiation that is piped through a waveguide flange 20. A modulator 22 within the magnetron 12 controls the beam duty cycle and switching of the beam from full power, e.g., 1500 Watts, to nil power. Preferably, the apparatus 100 includes a shield or another type of protection for the magnetron 12 from reflected energy, such as a T-waveguide component 24 located after the magnetron 12. The T-waveguide component 24 redirects all back-reflected microwave energy to a liquid-cooled black-box absorber 26. The apparatus 100 also may extract a small fraction of the applied power so that overall beam performance can be monitored. For example, part of the incident beam traversing the circulator, i.e., 0.1% power, impinges on a directional coupler of the cross guide type, and is passed to a coaxial Bird microwave watt meter used to monitor beam performance.

The transmitter section 100A further includes a tuner 14 that regulates the output beam and focusing horn 16 to direct the microwave frequency beam onto the ground. The 3-stub straight waveguide tuner component regulates the beam by controlling its forward and reflected power. Other capabilities of the apparatus 100 may include ways that the magnetron 12 reduces the beam sidelobes and sharpens the focus. As such, a horn antenna with Fresnel lens mounted to its outer rectangular opening passes the beam onto the ground. Side-lobe intensity of the beam exiting antenna is reduced by the horn-lens combination, delivering a focused elliptical imprint of 0.324 m$^2$ cross-sectional area at 0.95 m range. The magnetron source 10 with load, tuner, and recirculator waveguide components are products ASTEX, Inc., of Woburn, Mass.

The energy from the magnetron 12 is focused through a Fresnel lens manufactured by Seavey Engineering Associates, Inc., of Cohasset, Mass., into the ground across an approximately 20 cm diameter for rapid heating and the generation of a thermal gradient. Height, energy and time requirements for proper contaminate interrogation may be determined by those skilled in the art.

Receiver Section 100B

A means for reflecting liberated thermal emissions to the beam condenser 40 is located within the receiver section 100B that comprises a scanner assembly 42 having a scanner 44. The scanner assembly 42 permits constant field-of-view area ground coverage as the TTLS is in motion. The scanner 44 preferably comprises the rotating three-mirrored triangular ground scanner 46 to redirect thermal luminescence from the ground to the condenser. A mirror component of the three-mirrored triangular scanner 46 is centered on the irradiated area when the apparatus 100 is at a standstill. Rotational speeds of the scanner 44 are electronically synchronized with the linear transverse speed of a transport vehicle 92.

The scanner assembly 42 further includes a beam condenser 50. The beam condenser 50 reduces the scanner-reflected TL radiance 10x, from 25.4 cm to 2.54 cm beam diameter, collimates the condensed TL radiance, and directs it along the optical axis of the interferometer 52. Preferably, the condenser 50 comprises a narrow field-of-view telescope 54 that matches the scanner-reflected TL to the entry window of the interferometer 52. The condensed thermal luminescence is sent to the interferometer 52. The interferometer 52 provides the means to process the condensed liberated thermal emissions 40 interferometrically where interferograms are produced. The interferometer 52 rapidly measures the spectral energy content of the contaminant's thermal fingerprint, in the liberated thermal luminescence. It is preferred that the interferometer scan rate be maximum, with the spectral resolution of 2 cm$^{-1}$ or less. With this Michelson instrument, the scan rate was increased to a maximum of 33 Hz, for 2 cm$^{-1}$ spectral resolution. An example of the interferometer 52 includes the Michelson interferometer manufactured by Midac Cooperation of Irvine, Calif., under the tradename M2401-C. The scanner 44, condenser 50, and interferometer 52 optics are precision aligned to direct, condense and then process the liberated thermal luminescence from the irradiated ground.

By irradiating the surface and analyzing its liberated thermal luminescence, an enhanced 7.14–14.29 $\mu$m absorption and emission band signature of the contaminant occurs through a simple difference-spectrum measurement. The time window for conducting the spectral search opens as a thermal gradient develops in the irradiation zone, and closes as the gradient dissipates. The present invention generates, detects and processes TL radiant light in an optimum time frame for sensing chemical contamination of surfaces.

The amount of time it takes to build a sufficiently large thermal gradient to make the spectrum detection viable becomes problematic. Reduction of the heating time required to establish a detection event from several seconds to a subsecond period may be accomplished by increasing the scan rate of the interferometer, which increases the number of coadded interferograms per spectrum (signal-to-noise ratio, SNR, of the TL spectrum is proportional to the square root of the number of coadded interferograms). The modified commercial Michelson interferometer 52 to scan an order of magnitude higher, i.e., 33 Hz, was used to improve determination time periods. Increases in the scan rate, such as a doubling of scan rate to 66 Hz or beyond, further improves determination time periods. However, limitations of applying an inertial, moving mirror, interferometer to the TL detection problem exist. A photoelastic modulation (PEM) based Fourier transform infrared spectrometer where interferogram rates can exceed 10 KHz alleviates or eliminates the SNR problem.

The interferograms produced by the interferometer 52 are co-added in sets and Fourier transformed in contiguous sets to produce spectra. Subtracted spectra are numerically filtered, baseline-corrected, and checked for positive parity. The interferograms are then scaled and submitted to a neural network for pattern recognition of contaminant features in the thermal luminescence.

The preferred embodiment of contaminant determination occurs with data collection by the TTLS while traveling an open land area. Moving data collection is accomplished by an electronic monitoring of the scanner 44 that allows the synchronization of interferogram collections and speed of travel conditions, their Fourier transformation into spectra, the numerical filtration of spectra, parity check and subtraction of spectra, and pattern recognition stages of data handling. A serial communication protocol system with interrupt-driven I/O may be used to perform these tasks. Command and status transfers are routed between scanner controller, central computer, and the interferometer's direct memory access (DMA) board 56. Integrity of these data transfers is kept at a high level by software modules that control handshaking, packetization, and checksums operations.

TL directed from the microwave beam-irradiated zone is scanned interferometrically through linear movement of a reciprocating mirror inside a Michelson interferometer cube. The interference is manifest electronically as digital waveforms produced at a liquid-nitrogen-cooled photoconductive HdCdTe semiconductor surface or detection element 58 where TL radiance exiting the cube is focused. These complex time-domain waveforms are summed constructive and destructive interference intensities of the TL radiant light called interferograms. They are co-added, Fourier transformed into spectral amplitudes by a high-speed digital signal processor, and subtracted in contiguous spectral data sets in the TTLS data processing system.

A means to derive pattern recognition stages from the processed thermal emissions 60 includes a neural network. The neural network learnt mechanism having a mathematical inner product that is preferably conducted by the components of the output of the neural network, through feed-forwarding of pre-processed sensor spectra. Data processing through the interferometer's DMA board 56 moves digitized inteferograms into two computer memory buffer regions, at a rate of 33 Hz, to create a ping-pong effect. When buffer region 1 is full, an interrupt routine signals a DMA controller to start transferring newly collected interferograms into region 2 while a simultaneous coaddition operation is done in region 1. Sequential fast Fourier transformation (FFT, the Fourier transform operation computes a 1024 point complex FFT in about 0.0013 second by an array digital signal processing board), spectrum subtraction, parity, baseline correction and noise filtration operations follow in this same manner. This produces numerical files of difference spectra in a format proper for submission to the input layer of the neural network.

Pattern recognition by the network yields a yes/no decision making of surface contamination. The components of the actual contaminant vectors are used to train the neural network, while the value of the inner product is an alarm 62 indicator. When the inner product value is within a finite range close to 1, the alarm 62 trips. The alarm 62 may be in audio, visual and/or recordation form. Preferably the apparatus 100 includes an alarm 62 that records the location and intensity of the chemical contaminant with detection. Typically a Global Positioning System (GPS) 64 receiver is used to record determined locations of contaminated and non-contaminated surface areas. The recordation of the evaluated areas may be in terms of present/absent indications of contamination, or percentage probabilities of the likelihood of the presence (or absence) of the contaminants. These representations of the recordation of contamination may exist in number, shading or other like indicating form, with the type of indicating form determinable by those skilled in the art for a particular purpose.

Figure 2:
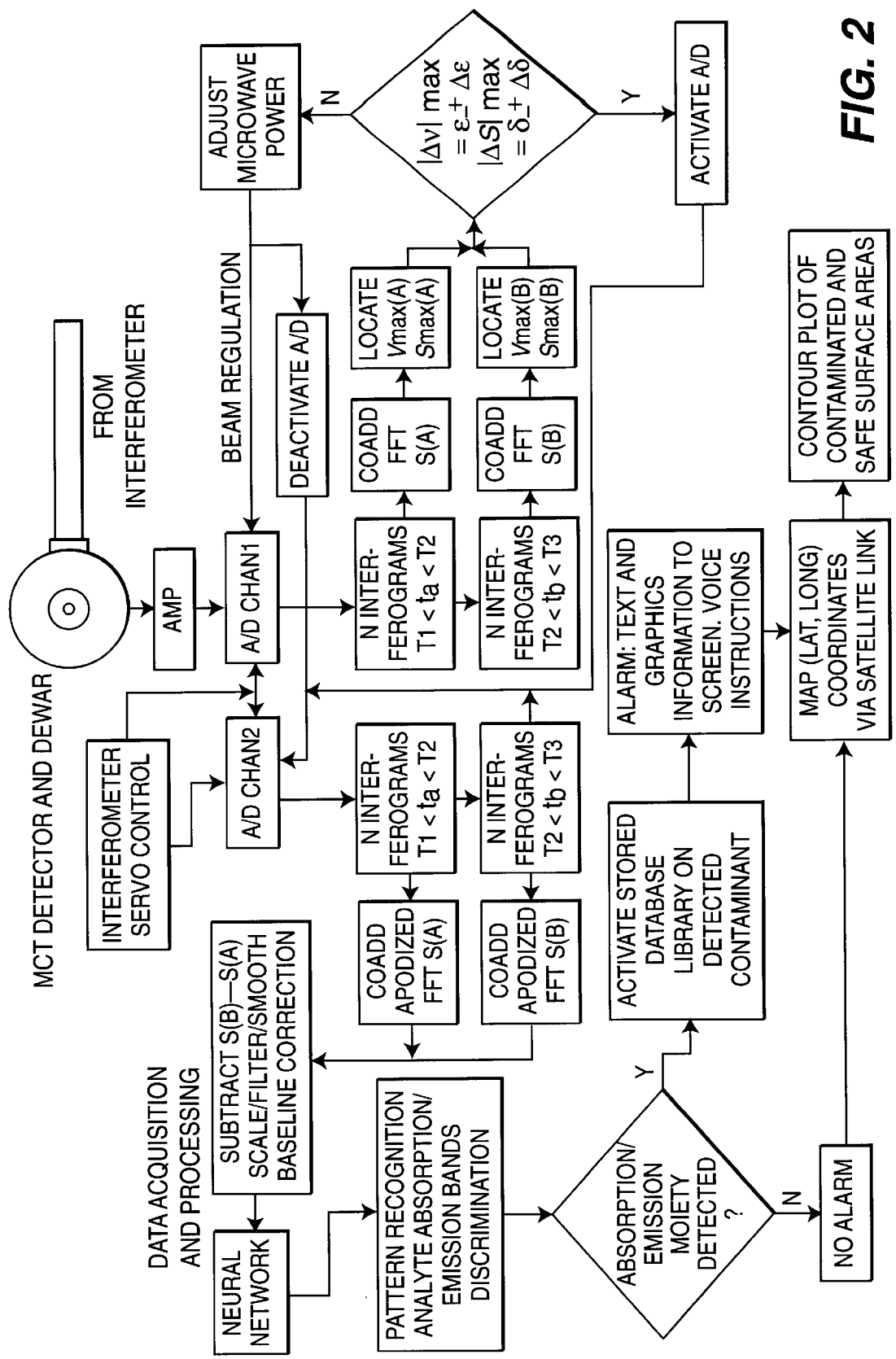
FIG. 2 is an operational flowchart of the TTLS data acquisition and processing system with feedback loop for the present invention.

FIG. 2 illustrates an operational flowchart of the TTLS data acquisition and processing system with feedback loop of the present invention. Scanned radiant emissions directed from the surface are directed to and operated on by a Michelson interferometer, producing interference waveforms that are amplified and digitally recorded. The right-side and middle section of the chart shows how the TTLS beam source is regulated to produce maximum TL flux from the irradiated ground within intensity limitation. The left-side and middle sections depict how raw interferograms sets are co-added and transformed into thermal spectra then prepared for submission to a neural network pattern recognition system. The bottom section shows post-processing events including GPS localization of the contaminant area and instructions on how to deal with the threat.

The amplified and modulated voltage waveform, from TL radiance exiting the interferometer cube and focused onto the cooled infrared photoconductive MCT detector chip as shown, is first conducted to two parallel analog-to-digital circuits (ADCs), as activation of the ADC is synchronized to movement by the rotating ground scanner. Located after the ADCs are storage buffers for Graybody spectra M(A) and M(B). The Graybody spectrum M(A) is derived from the Fourier transform of the coadded interferogram set measured in heating period $T1 \leq T \leq T2$. Likewise, M(B) is computed within the period $T3 \leq T \leq T4$. M(A) and M(B) are relative "cold" and "hot" Graybody spectra, respectively, and the full period $T1 \leq T \leq T4$ accounts for 1 difference-spectrum measurement as the ground scanner rotates about $2\pi/3$ radians, giving three detection events per full rotation.

The modules to the right side of FIG. 2 show how the TTLS magnetron regulates beam power so as to produce ideal heating of the ground (maximum thermal gradient). Two pieces of information are extracted from M(A) and M(B): their Graybody maximum spectral intensity $M_{max}$ and the corresponding energy at this peak intensity $V_{max}$. The absolute difference values $\delta = |M_{max}(B) - M_{max}(A)|$ and $\epsilon = |V_{max}(B) - V_{max}(A)|$ are tested with tolerance $(\Delta\delta, \Delta\epsilon)$. When the values are low the beam power is increased; when the values are high the beam power is decreased.

Figure 3:
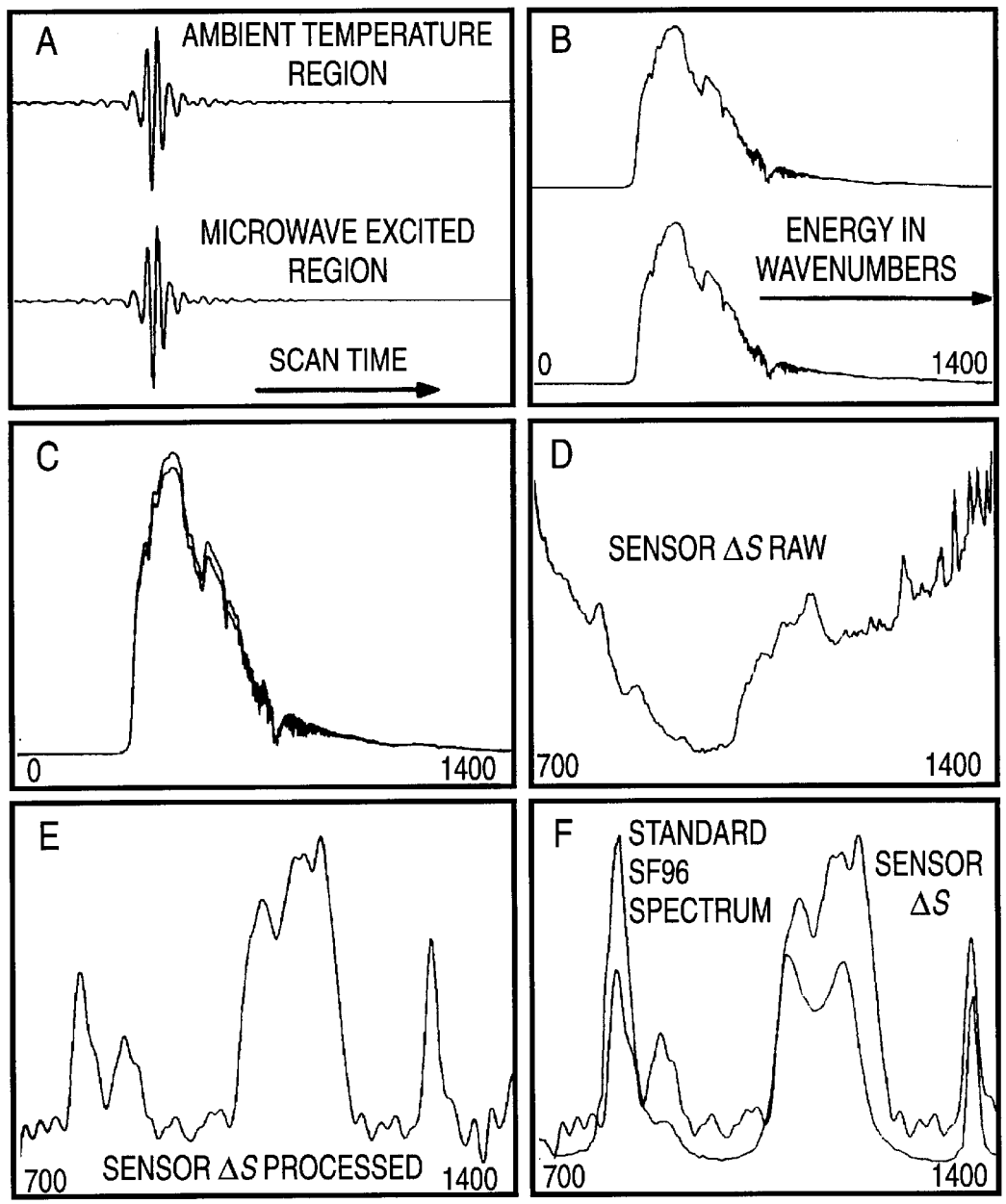
FIG. 3 illustrates acquisition and preprocessing of TTLS data from FIG. 2 before submission to the neural network for the present invention.

Modules to the left side of FIG. 2 perform a succession of operations: apodization on the raw interferograms, subtraction of spectra M(A)–M(B), filtered baseline-correction of difference-spectrum, and its polarity check and positive correction (the difference spectrum can have negative or positive parity). This preprocessing is graphically illustrated in FIG. 3, where various stages of data processing from a soil sample wetted by polydimethyl siloxane, a simulant of nerve agent VX, are shown. Data reduction by the TTLS involves a neural network system performing precise spectral pattern recognition of select chemical compounds it is trained against. Implemented in either hardware (neural network ETANN or Ni1000 chips) or software (C++ code) computer models, the network input layer accepts preprocessed spectra (one node per spectral amplitude spanning 7.14 $\mu$m to 14.29 $\mu$m, or 350 nodes for 2 wavenumber resolution) from the sensor's final data processing module. The neural network architecture is designed with 2-hidden layers of nodes, between input and output layers, where the number of nodes per layer are relevant to training speed, convergence, and prediction performance. Final training with this architecture produced a finely tuned weight matrix that serves as the TTLS pattern recognition filter.

Through feed forwarding of sensor spectra through the weight matrix via the network input layer, real numbers are presented at the output layer. These analog data nodes represent components of a vector whose dimension is the number of nodes. A vector may be constructed from the presented output node components (T). A normal inner product $\sigma = (T \cdot R_i)/N$ is then computed, when $R_i$ are the basis vectors of the chemical contaminants used to train the network and N is the norm for each inner product $(t_1 r_1 + t_2 r_2 + t_3 r_3 + \ldots + t_n r_n)^{1/2}$. If the quantity $\sigma$ lies within some set interval, typically $1 \leq \sigma \leq 0.98$, than the alarm 62 will trip. Results of exhaustively training the 4-layer neural network of 350-256-129-9 architecture indicated better than 99% true positive and nearly zero false positive results in actual sensor data, where the network comprised nine chemical absorption spectra of liquid agent and simulant materials as the training and validation data sets.

In the event an alarm signal is triggered, shown as block "absorption/emission moiety detected" in FIG. 2, several sensor specific tasks such as routing reports on the contaminant properties, GPS mapping of the contaminated terrain, and procedures on how to deal with chemically contaminated scenarios are activated in the TTLS.

As seen in FIGS. 3A–3F, pre-processing of the TTLS data comprises several steps. FIGS. 3A–3F illustrate TTLS stages of data collection and processing leading to a $\Delta S$ measurement from soil that is wetted by polydimethyl siloxane (SF96), a simulant of nerve agent O-ethyl S-2diisopropylaminoethylmethylphosphonothiolate (VX). Sensitivity of detection was a few droplets (0.3 ml/drop) dispersed over 127 cm$^2$ surface area. Accuracy of detection with the TTLS is also improved, i.e., fewer false alarms, because a full data spectrum is measured and analyzed, compared with lidar detection performed by scattering at two or a few discrete wavelengths of a $CO_2$ laser.

Referring to FIG. 3A, several interferograms are co-added from the ambient temperature region as well as the region excited by microwaves. The emissivity contrast between heated and ambient zones reveals spectral identity of the surface contaminated. Fourier transforms are calculated, as seen in FIG. 3B, from the co-added interferogram sets allow frequency-domain analysis of a small emission signal given off by SF96. The effect of the localized heating is apparent in the Graybody shift shown in FIG. 3C. The two similar Fourier transforms are subtracted to reveal a small emission contrast between ground and SP96. In FIG. 3D, the difference spectrum reveals infrared emission or absorption bands by SF96 in the stimulated thermal non-equilibrium state of the irradiated surface. After several specialized algorithms are applied to the raw difference spectrum, as seen in FIG. 3E, spectral identity of the contaminant becomes clearly evident. Finally, the difference spectrum is fed and forwarded through the TTLS's neural network for a yes/no detection decision. The sensor's preprocessed difference spectrum is shown in FIG. 3F against a SF96 standard spectrum, where an alarm trips against the SF96. FIG. 3F further shows the presence of a second contaminant.

As seen in FIG. 3F, there exists a concern with the TL sensing method, as is the case for all similar remote-sensing schemes, on how to deal with spectral interferences from compounds overlapping some or all absorption bands of a targeted analyte, e.g., absorption band overlap between analytes in the 7.14–14.29 $\mu$m spectrum. Retraining the neural network with additional mixture-spectrum features, and thereby expanding its weight matrix to accommodate such analyte mixtures, as well as additional preprocessing to narrow the spectral features in AS over the interferometer's optical bandwidth may be used to overcome these problems. For example, an operation called Fourier self-convolution may be added after the final filtration stage of preprocessing to determine all overlapping principal bands $\Delta S$.

The transport vehicle 92 may include any suitable vehicle for transporting the apparatus 100, with the proper vehicle selection being determinable by those skilled in the art. Preferably, the transport vehicle 92 comprises the United States Army's Highly Mobile Multipurpose Wheeled Vehicle, known as HMMWV, towing a trailer 92A modified to accommodate the optical sensor head 102. The optical sensor head 102 is preferably mounted onto a modified M116A2 military trailer 92A using a pedestal. With this arrangement, the modified trailer 92A provides a shelter that houses data handling and automation control electronics, environment regulation equipment, a global positioning system 64, radio communications and other like supporting equipment for the apparatus 100. The supporting equipment may include electrical power supplied by a DC generator mounted in the HMMWV engine compartment, a DC battery bank located in a side compartment of the vehicle 90, and a DC to AC converter housed inside the shelter. Maps of the threat contaminant areas through post-processing of thermal luminescence data integrated to the Global Positioning System (GPS) 64 are produced, with communication of this location data transmitted through radio links to an outside receiving station.

In addition to being mobile, i.e., functions on the move, the apparatus 100 of the present invention also is self-contained having all subsystems are integrated, with power generated and distributed on board. Preferably, the apparatus 100 possesses tactical, i.e., automated computer intercommunication and radio extracommunication systems. As such, the apparatus 100 uses a low cost, continuous-wave, shielded magnetron source to liberate heat from suspect surfaces without posing a radiation health hazard. The apparatus 100 further provides a system for detecting contamination layers on terrestrial surfaces in situ by analyzing stimulated infrared emissions for their fingerprint spectra. This is accomplished by the apparatus 100 in near real-time with the sensor stationary or while it operates on the move.

Figure 4:
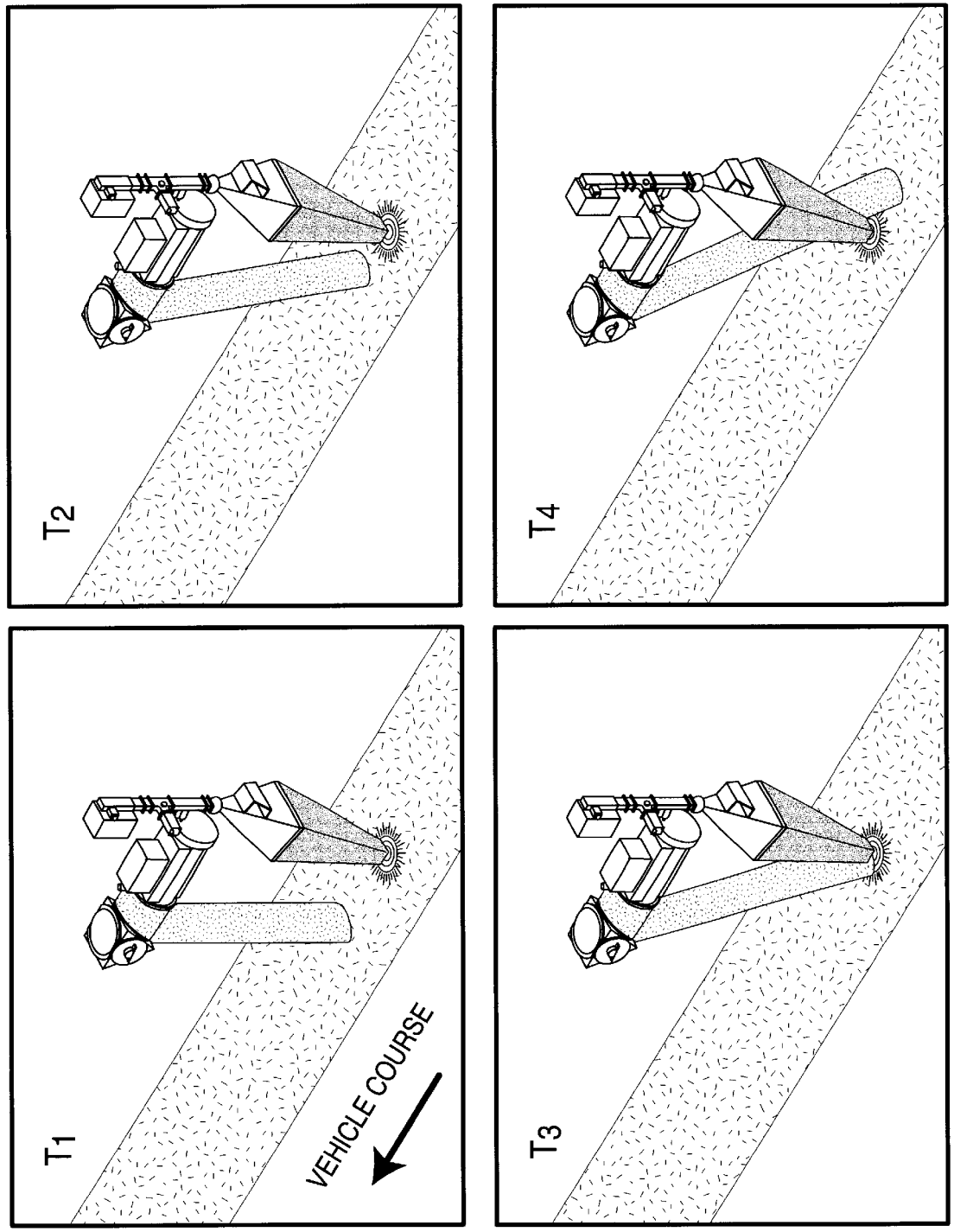
FIG. 4 illustrates the TTLS of the present invention in operation.

In operation, as seen FIG. 4, chemical contamination of terrestrial landscapes and manmade surfaces is determined by irradiating a suspect surface with a high powered microwave or near IR frequency beam, reflecting and condensing liberated thermal emissions, processing the condensed liberated thermal emissions and deriving pattern recognition stages from the processed thermal emissions. The receiver section 100B as a unit is housed in an inner cradle, shock-mounted to an outer frame of the housing assembly 90, and isolated from the sensor transmitter section 100A. Its triangular scanner, belt-to-pulley driven about a central axle and camshaft, comprises three flat 12" diameter mirrors coaxially centered and oriented 120° apart. Scanner rotational velocity ($\omega$) is relative to the sensor's linear speed (v), providing a constant field-of-view (FOV) of a (downward looking) fixed ground object. When the TTLS is at a standstill, the scanner is fixed in position with FOV centered on the irradiated area, being the scanner home position. While the sensor head is in tow, a microprocessor controller continuously probes the HMMWV speedometer encoder while relaying feedback to the scanner driver motor. This controller system is equipped with an electronic board that compares two sets of pulses—one pulse rate is proportional to the velocity of the towing vehicle v and the other to the rotational speed of the scanner $\omega$. Regulation of $\omega$ is accomplished as the ratio of pulse rates is maintained at unity, i.e., $d(\sec^2\theta)|\omega|/|v|=1$; where d=1.70 m is the perpendicular distance from scanner axis to ground object, and the scan angle range is $0°\leq\theta\leq 40°$. Pulse-ratio computing is performed very 200 ms to assure a smooth and accurate tracking of the fixed ground object by the scanner's motor driver. The surface is irradiated with a high powered microwave frequency beam in the W-band of from about 2.100 GHz to about 3.450 GHz, that is controllable to produce regulated thermal heating of a surface. The regulated thermal heating is synchronized with the rotational speed of a scanner, the linear transverse speed of a transport vehicle 92, the electronic data acquisition of thermal luminescence interferograms, the preprocessing of thermal luminescence spectra and the neural network pattern recognition by a computer. The synchronization is designed to collect thermal luminescence data during a thermal window having a maximum temperature gradient along the irradiated surface. Once collected, processing occurs when collected thermal luminescence is conditioned into Fourier transformations and the Fourier transformations are converted into spectra that is numerically filtered. The microwave irradiating the ground is regulated to produce an opportune thermal heating of the surface. This occurs during a thermal window when a temperature gradient that builds on the irradiated surface becomes maximum.

As further seen in FIG. 4, radiant emissions directed by the scanner from the constant FOV ground object to a 10x's beam condenser—a narrow FOV Newtonian telescope with 12" diameter clear aperture primary spherical mirror. A collimated 2.54 cm diameter beam exiting the condenser is directed to a MIDAC M2401-C Michelson interferometer cube. The variant flat mirror of the interferometer was made to oscillate at 33 Hz (interferograms per second) whereby a succession of fast Fourier transformations (FFTs) is done on co-added interferogram sets by hardware and software modules onboard the TTLS. A string of contiguous spectra are stored in computer RAM memory during one measurement cycle representing ⅓ scanner rotation, with 2 wavenumbers of resolution. They are dynamically stored into memory bins, where adjacent spectra are subtracted and sequentially submitted to a fully trained neural network recognition system. Training of the network is performed against several signature spectra of contaminants targeted for detection. In this manner, three detection decisions are made per full revolution of the receiver's rotating ground scanner. Real-time detection and identification of chemical contaminants on a surface becomes attainable with the present invention.

Figure 5:
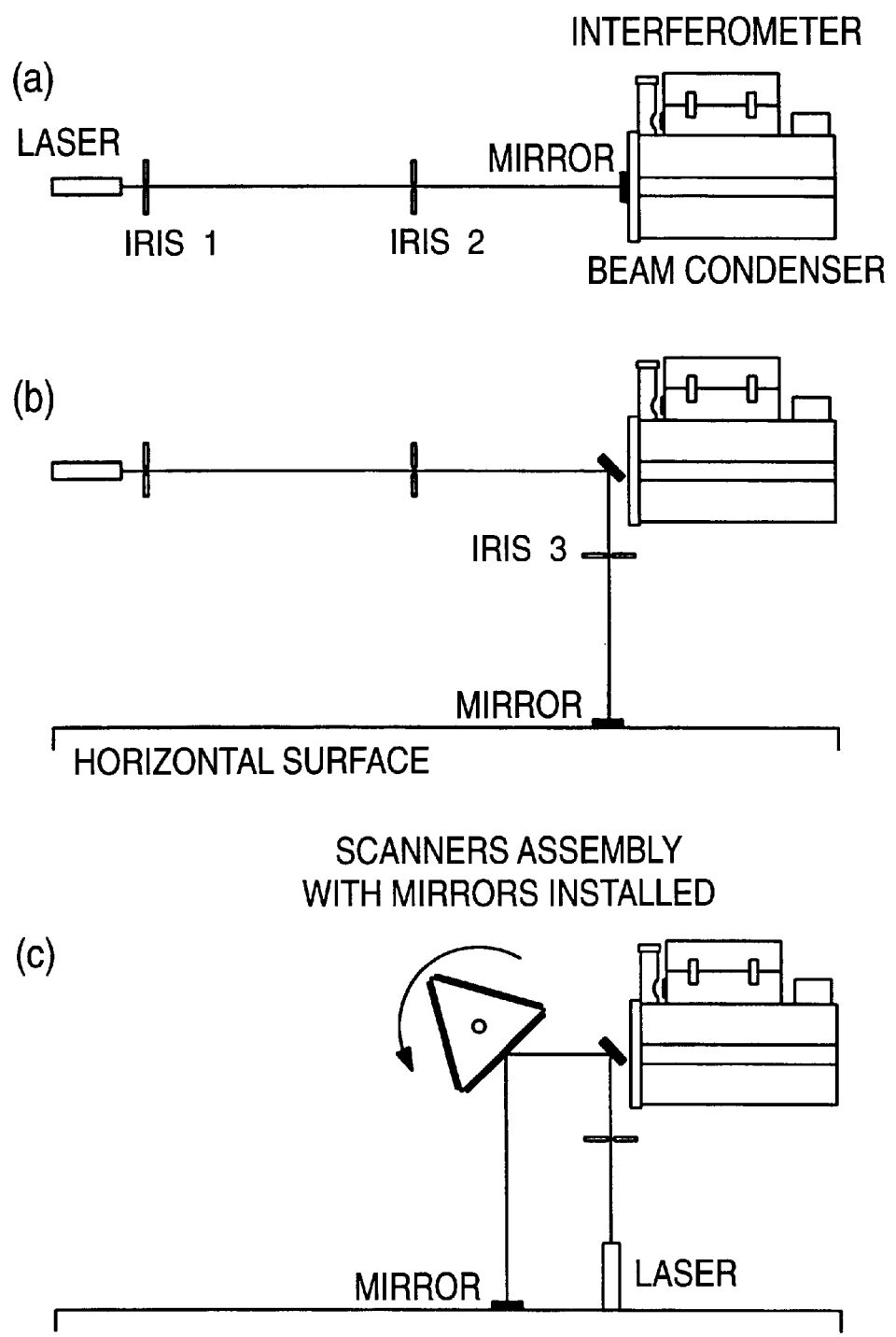
FIG. 5 illustrates optical alignment of the TTLS receiver conducted in three phases.

Optical alignment of the TTLS receiver is conducted in three phases as shown in FIG. 5. The three-step optical alignment of the TTLS receiver is done by a series of retroreflections by a He—Ne laser beam. First, the condenser's primary mirror optical (horizontal) axis is established by retroreflecting a HeNe alignment beam that is directed to its center of curvature. The alignment beam is incident to a flat mirror mounted to the telescope's spider vertical frame (the spider is a radial mount for 90° central flat reflector in the Newtonian telescope) incident from the left, as shown in step A. Two pinhole irises 1 and 2 are positioned in the superimposed incident and reflected beams. Second, the perpendicular (vertical) axis is established by inserting a 90° reflector in the horizontal beam, just before the condenser, and retroreflecting it from a flat horizontal mirror on the optics table, as shown in step B, to define iris 3. Third, the triangular scanner structure is placed on its mount, and the alignment beam is reversed and made to pass through iris 3, reflect 90° twice, then retroreflect by another horizontal flat mirror, as shown in step C. Finally, the scanner is rotated in increments of 120° and any necessary orientation adjustments to its three mirror disks are made so that incident and reflected beams are superimposed. An alignment tolerance of approximately 0.0635" for centering the pinhole irises has been demonstrated.

With the mirrors correctly positioned, annular rings on the scanner's timing gear, with magnetic sensors, define start-of-scan orientation (home), crossover, and end-of-scan positions. With these reference settings known, and with the pulse ratio tracking circuit actively tracking the sensor velocity, a microcomputer controller can easily compute and update ω to the 35-pound scanner in millisecond periods. This provides a smooth and precise tracking of the object (ground) area as the HMMWV velocity changes in its course of travel.

EXAMPLE

A TTLS having a magnetron, scanner assembly, condenser, and interferometer is placed in motion. The magnetron projects a microwave frequency beam of 1.5 W cm$^{-1}$ onto the ground. The scanner assembly tracks a fixed area of 978.5 in$^2$ on the ground and projects liberated thermal energy from that area of a 10×'s beam condenser, a Newtonian telescope with 12" diameter primary mirror. The condensed 1.2" radiant beam is directed to a Michelson interferometer where interferograms are produced, co-added and Fourier transformed for a TL spectral signature search of the surface contaminant.

The magnetron beam power is controlled to vary the output so as to produce a sufficiently large Graybody shift by the irradiated ground. Data is collected before and after the scanner's field-of-view intercepts the irradiated area.

Fourier transforms of co-added interferograms, collected in and out of the irradiated zone when the thermal gradient is maximum, are subtracted. This difference spectrum contains the infrared absorption or emission bands of the chemical contaminant and is electronically preprocessed and sent to a neural network for pattern recognition and yes/no detection decision making.

The foregoing summary, description, example and drawings of the present invention are not intended to be limiting, but are only exemplary of the inventive features which are defined in the claims.

What is claimed is:

1. A method for determining chemical contamination of terrestrial landscapes and manmade surfaces using thermal luminescence, comprising:

irradiating a surface having contaminated material with a high power microwave frequency beam of such frequency as to generate a maximum thermal gradient in the surface and to be highly absorbed by the surface having contaminated material, the contaminated material being capable of absorbing irradiation in the near, far and middle portions of the infrared spectrum and liberating thermal emissions from the surface;

reflecting and condensing the liberated thermal emissions to form condensed liberated thermal emissions;

detecting in the middle portion of the infrared spectrum and processing the condensed liberated thermal emissions in the middle portion of the infrared spectrum to form processed liberated thermal emissions; and, deriving pattern recognition stages from the processed liberated thermal emissions.

2. The method of claim 1, wherein the step of reflecting and condensing liberated thermal emissions includes reflecting thermal luminescence data during a thermal window having a maximum temperature gradient along the irradiated surface.

3. The method of claim 1, wherein the condensed liberated thermal emissions are detected and processed when the thermal gradient is maximum.

4. The method of claim 1, wherein the high power microwave frequency beam is controlled to produce regulated thermal heating of a surface.

5. The method of claim 1, wherein the condensed liberated thermal emissions are detected and processed only during the period when $\partial^2 T_s/\partial t^2=0$, where $T_s$ is surface temperature and t is irradiation time.

6. The method of claim 1, wherein the frequency of the high power frequency beam is from about 2.10 GHz to about 3.45 GHz.

7. The method of claim 1, wherein the frequency of the high power frequency beam is 2.45 GHz.

8. The method of claim 1, wherein the step of reflecting and condensing liberated thermal emissions includes scanning liberated thermal emissions with a scanner having a rotatable mirrored receiver and directing the scanned thermal emissions to a condenser optic and an interferometer.

9. The method of claim 1, wherein the step of detecting and processing the condensed liberated-thermal emissions includes producing interferograms, co-adding the interferograms in sets, and Fourier transforming the co-added interferograms in contiguous sets to produce spectra, wherein subtracted spectra are numerically filtered, baseline-corrected, checked for positive parity, and scaled.

10. The method of claim 1, wherein the step of deriving pattern recognition stages from the processed thermal emissions includes submitting the processed liberated thermal emissions to a neural network for pattern recognition of contaminant features in the thermal luminescence.

11. The method of claim 10, wherein the neural network uses actual contaminant vectors to train the neural network for formulating an alarm indicator.

12. The method of claim 1, wherein the method is performed in real time.

13. An apparatus for determining chemical contamination of terrestrial landscapes and manmade surfaces from the analysis of induced thermal spectra by employing thermal luminescence, comprising:

means for irradiating a surface having contaminated material with a high power microwave frequency beam of such frequency as to generate a maximum thermal gradient in the surface and to be highly absorbed by the surface having contaminated material, the contaminated material being capable of absorbing radiation in the near, far and middle portions of the infrared spectrum and liberating thermal emissions from the surface;

means for reflecting and condensing liberated thermal emissions to form condensed liberated thermal emissions;

means including an interferometer for detecting in the middle portion of the infrared spectrum and processing condensed liberated thermal emissions to form processed liberated thermal emissions; and means for deriving pattern recognition stages from the processed thermal emissions.

14. The apparatus of claim 13, wherein the irradiating means includes a magnetron.

15. The apparatus of claim 13, wherein the frequency of the microwave frequency beam is in the range from 2.1 to 3.45 GHz.

16. The apparatus of claim 13, wherein the frequency of the microwave frequency beam is 2.45 GHz.

17. The apparatus of claim 13, wherein the means for detecting and processing the condensed liberated thermal emissions is operative when the irradiating means attains the maximum thermal gradient on the surface being irradiated.

18. The apparatus of claim 13, wherein the means for detecting and processing the condensed liberated thermal emissions is operative during a period when $\partial^2 T_s/\partial t^2=0$, where $T_s$ is the surface temperature and t is irradiation time.

19. The apparatus of claim 13, wherein the means for reflecting and condensing liberated thermal emissions includes a scanner having a sensor and a condenser optic spaced from the scanner, wherein the scanner directs reflected thermal emissions along a constant field-of-view to the condenser optic when the apparatus is in motion.

20. The apparatus of claim 19, in combination with a linearly transversely movable transport vehicle upon which the apparatus rests, wherein the scanner includes a rotatable mirrored receiver and means for electronically synchronizing the rotational speed of the mirrored receiver with the linear transverse speed of a transport vehicle.

21. The apparatus of claim 20, wherein the scanner has a three-mirrored triangular configuration.

22. The apparatus of claim 13, wherein the means for reflecting and condensing liberated thermal emissions includes a scanner and a condenser, and wherein liberated thermal emissions reflected by the scanner are condensed in the condenser for ingress into the means for detecting and processing the condensed liberated thermal emissions.

23. The apparatus of claim 13, including an alarm connected to the deriving means and capable of warning of the occurrence of the detection of a chemical contaminant.

24. The apparatus of claim 13, including a Global Positioning System connected to the deriving means, wherein the location of surfaces having contaminated material is registered.

25. An apparatus for determining chemical contamination of terrestrial landscapes and manmade surfaces from the analysis of induced thermal spectra by employing thermal luminescence, comprising:

means for irradiating a surface having contaminated material with a high power microwave frequency beam of such frequency as to generate a maximum thermal gradient in the surface and to be highly absorbed by the surface having contaminated material, the contaminated material being capable of absorbing radiation in the near, far and middle portions of the infrared spectrum and liberating thermal emissions from the surface;

means for reflecting and condensing liberated thermal emissions to form condensed liberated thermal emissions including a scanner and a condenser comprising a narrow field-of-view telescope capable of condensing reflected liberated thermal luminescence by a factor of approximately 10, wherein liberated thermal emissions reflected by the scanner are condensed in the condenser;

means for detecting in the middle portion of the infrared spectrum and processing liberated thermal emissions reflected by the scanner and condensed in the condenser to form processed liberated thermal emissions; and means for deriving pattern recognition stages from the processed thermal emissions.

26. The apparatus of claim 25, wherein the irradiating means includes a magnetron.

27. The apparatus of claim 25, wherein the frequency of the microwave frequency beam is in the range from 2.1 to 3.45 GHz.

28. The apparatus of claim 25, wherein the frequency of the microwave frequency beam is 2.45 GHz.

29. The apparatus of claim 25, wherein the means for detecting and processing the condensed liberated thermal emissions is operative when the irradiating means attains the maximum thermal gradient on the surface being irradiated.

30. The apparatus of claim 25, wherein the means for detecting and processing the condensed liberated thermal emissions is operative during a period when $\partial^2 T_s/\partial t^2=0$, where $T_s$ is the surface temperature and t is irradiation time.

31. The apparatus of claim 25, wherein the means for reflecting and condensing liberated thermal emissions includes a scanner having a sensor and a condenser optic spaced from the scanner, wherein the scanner directs reflected thermal emissions along a constant field-of-view to the condenser optic when the apparatus is in motion.

32. The apparatus of claim 31, in combination with a linearly transversely movable transport vehicle upon which the apparatus rests, wherein the scanner includes a rotatable mirrored receiver and means for electronically synchronizing the rotational speed of the mirrored receiver with the linear transverse speed of a transport vehicle.

33. The apparatus of claim 32, wherein the scanner has a three-mirrored triangular configuration.

34. The apparatus of claim 25, including an alarm connected to the deriving means and capable of warning of the occurrence of the detection of a chemical contaminant.

35. The apparatus of claim 25, including a Global Positioning System connected to the deriving means, wherein the location of surfaces having contaminated material is registered.

* * * * *